United States Patent
Sander et al.

(10) Patent No.: US 7,286,992 B2
(45) Date of Patent: Oct. 23, 2007

(54) VOICE CONTROL SYSTEM FOR SURGICAL MICROSCOPES

(75) Inventors: Ulrich Sander, Rebstein (CH); Michael Lippe, Winter Haven, FL (US); Ohm Savanayana, Au (CH); Juergen Engl, Neu-Ulm (DE); Andreas Tedde, Hinterforst (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 813 days.

(21) Appl. No.: 10/459,146

(22) Filed: Jun. 11, 2003

(65) Prior Publication Data
US 2004/0034534 A1    Feb. 19, 2004

(30) Foreign Application Priority Data
Jun. 14, 2002  (DE) ................. 102 26 539

(51) Int. Cl.
G10L 21/00   (2006.01)
(52) U.S. Cl. ..................................... 704/275
(58) Field of Classification Search ............... 704/275, 704/270, 271, 272; 381/110
See application file for complete search history.

(56) References Cited

U.S. PATENT DOCUMENTS

| 4,989,253 A * | 1/1991 | Liang et al. ................ 381/110 |
| 5,544,654 A * | 8/1996 | Murphy et al. ............. 600/443 |
| 6,278,975 B1 * | 8/2001 | Brant et al. ................. 704/275 |

OTHER PUBLICATIONS

SIOS (Siemens Integrated OP System; A. Schafmayer, D. Lehmann-Beckow, M. Holzner, "The Process-optimized operating room" in electromedica 60/2000 No. 2).
Katalavox—Voice-control used in Microsurgery since 1984—Katalavox, Sunnyvale, CA.

* cited by examiner

*Primary Examiner*—Susan McFadden
(74) *Attorney, Agent, or Firm*—Hodgson Russ LLP

(57) ABSTRACT

A control apparatus, in particular for a surgical microscope (8), has a voice operating unit (2) and at least one other operating unit such as a manual operating unit (4), a foot-controlled operating unit (5), and/or an eye-controlled operating unit (7). The control apparatus executes one set of microscope functions via the voice operating unit (2) and another set of microscope functions via the non-voice operating units (4, 5, and/or 7).

14 Claims, 1 Drawing Sheet

VOICE CONTROL SYSTEM FOR SURGICAL MICROSCOPES

CROSS REFERENCE TO RELATED APPLICATIONS

This application claims priority to German patent application 102 26 539.9, filed on Jun. 14, 2002, which is incorporated by reference herein.

FIELD OF THE INVENTION

The invention concerns a voice control system, e.g. for surgical microscopes.

BACKGROUND OF THE INVENTION

Voice control systems are being introduced into every kind of control system of machines, equipment, and computers, and are very useful especially in instances where hands or fingers are used for concentrated work. In the field of medicine and especially in the field of surgical microscopes, it is additionally desirable on the one hand not to interrupt concentrated and precise work with the hands, but on the other hand to avoid any unnecessary extension of very strict sterility requirements.

The latter consideration, in particular, is addressed by the SIOS (Siemens Integrated OP System; A. Schafmayer, D. Lehmann-Beckow, M. Holzner, "The process-optimized operating room" in electromedica 60/2000 No. 2), since with this, by means of a voice control system as an option for sterile remote control, functions in and around the operating room region can be controlled by voice, i.e. with no need for an operator, in either the sterile or the non-sterile area, to take the action him- or herself. This known voice control system does not, however, encompass the surgical microscope itself.

In order not to interrupt the surgeon's hands at their work, solutions using foot pedals have also been implemented. These had the disadvantage, however, of negatively affecting the surgeon's stable stance that is necessary for precise work. An increased need therefore existed for implementation of voice control systems for controlling surgical microscopes.

To prevent incorrect commands from being executed specifically in highly sensitive contexts, speaker-dependent systems (e.g. "Katalavox" of Kempf, Sunnyvale, Calif., U.S.A.) have been developed which function reliably even in loud environments.

All known voice control systems also extend to so-called continuous functions, whether raising or lowering an operating table, dimming an illumination system, orienting accessories, or zooming or focusing. In the context of these continuous functions, however, it has proven to be disadvantageous to arrive at the desired destination point, in stepwise fashion and with a cumbersome number of instructions, by repeating the spoken command. The risk also existed of too easily going beyond the desired point with one whole step. It has proven desirable to be able to move quickly toward the intended destination point from a great distance, and then to approach the point as slowly and precisely as possible. Contrasting with these are so-called "on-off" functions, which can be operated very effectively using the voice control system.

SUMMARY OF THE INVENTION

It is thus the object of the invention not to dispense with the advantages of a voice control system, but additionally to improve the control of continuous functions.

This object is achieved by resorting to a (preferably optional) manual control system and/or foot- or eye-controlled system in which, however, according to the present invention, invocation of the higher-order function is performed by means of voice control. The latter is not, however, to be regarded as a mandatory embodiment for purposes of the present invention.

According to the present invention, the "on-off" functions are to be performed using a voice operating unit, whereas the continuous functions are to be selected or invoked by means of the operating unit but the function itself is to be performed by pushing buttons on the handle or by way of foot pedals or the like (e.g. also by eye control).

A preferred embodiment of the invention provides for the voice control system to have a voice operating module remotely located with respect to a control unit and the surgical microscope. Decoupling of the voice operating module from the control unit and the surgical microscope yields the advantage that only the voice operating module, or conversely only the control unit or surgical microscope, needs to be sterilized. The sterile surgeon would thus, for example, be able to activate the surgical microscope, which is still prepared outside the sterile area by the operating room nurses, beforehand by means of the voice operating module, and to make the desired settings beforehand.

As soon as the voice operating module is active, all the functions of the surgical microscope can be invoked and, according to the present invention, certain functions such as e.g. the zoom or focus function can then be operated by way of the keypad on the handle or the foot controller, or by eye control. According to the present invention, the operating procedure for the surgeon is as follows: he or she switches on the voice operating module by voice command, e.g. "Voice control on." He or she then invokes the zoom function, e.g. "Zoom," and is then able to operate the zoom by manual, foot, or eye controller, but (optionally, according to a preferred embodiment) not with the voice control system.

On the other hand, in a further preferred embodiment of the invention a "standby" mode of the voice operating unit is also provided, in which all the functions of the surgical microscope, even in the event of a failure of the voice control system, can be operated conventionally by manual and/or foot and/or eye controller.

Another embodiment of the invention provides for the voice operating unit to be switched, with a certain voice command, into a mode in which the continuous functions are executed as long as a certain sound (vowel), perhaps also additionally speaker-identified, is being uttered. As soon as vocalization of that sound is halted, execution of the selected function is immediately stopped. Different sounds or different pitches correspond to different speeds of execution of the function. It is also possible for the voice operating module to be connected to the control unit via an electronic data line, in particular via a CAN bus and/or via light guide and/or a transmit/receive connection preferably with radio and/or light waves, in particular in the infrared region.

Further embodiments of the invention are described in the appended claims.

BRIEF DESCRIPTION OF THE DRAWING

The invention will be explained further, symbolically and by way of example, with reference to a sole figure, namely FIG. 1, which schematically depicts the arrangement of the voice control system, the operating menu display, the manual, foot, and eye control systems, the control unit, and the surgical microscope.

DETAILED DESCRIPTION OF THE INVENTION

Figure 1:
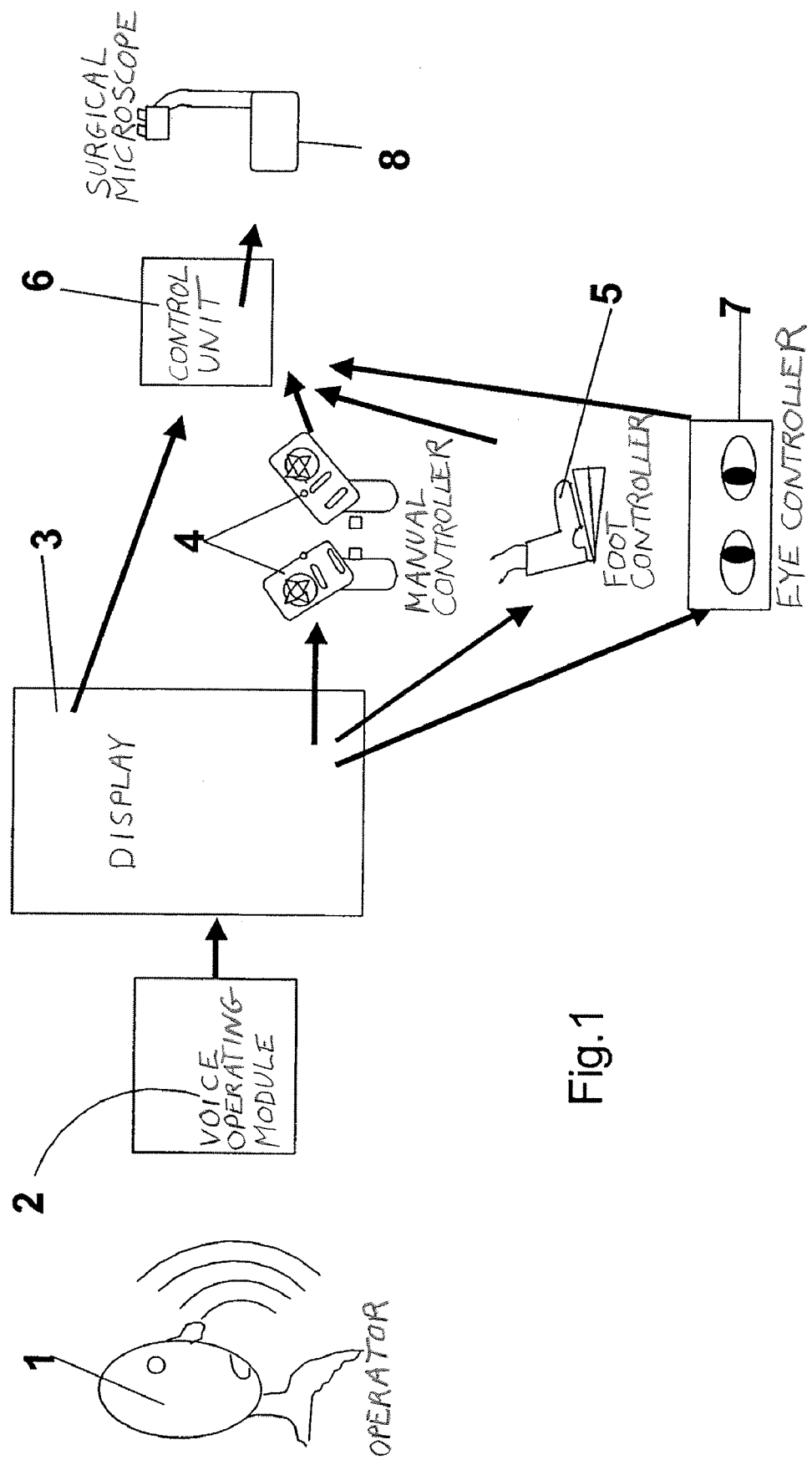

FIG. 1 shows a voice control apparatus for enabling a surgeon or other operator 1 to control a surgical microscope 8. The control apparatus comprises a voice operating module 2 including a microphone (not shown) for receiving voice commands, a display 3 for presenting an operating menu of voice commands, a manual operating module (handles) 4, a foot-controlled operating module 5, and an eye-controlled operating module 7. The voice operating module 2, as well as the other operating modules 4, 5, and 7, are connected to a control unit 6 which in turn is in communication with surgical microscope 8 to control various functions thereof.

It is apparent from the sole figure that an operator 1 can invoke an operating command from the menu displayed on display 3 by way of a voice operating module 2. Surgical microscope 8 has a first set of controllable functions that are activated directly by control unit 6. For example, these may be "toggle" type functions with two discrete settings such as "on" or "off". Surgical microscope 8 further has a second set of controllable functions that can be thought of as continuous functions in that the function settings are substantially continuously variable through a range of settings. For example, these may be positioning the surgical microscope, dimming an illumination system, orienting accessories, zooming or focusing. In one embodiment, a distinction must be made between functions in the first set in which control unit 6 is activated directly and functions in the second set, wherein a particular function is selectable through voice control unit 2 but operable by using handles 4, foot-controlled operating module 5, or eye-controlled operating module 7 to activate control unit 6 connected to surgical microscope 8.

Preferably, voice operating module 2 is remotely located with respect to control unit 6 and surgical microscope 8. This is beneficial because a sterile surgeon could activate the surgical microscope and perform preadjustment while the surgical microscope is still being prepared outside the sterile area by the operating room nurses. Conversely, a not yet sterile surgeon could perform adjustments with respect to an already sterilized surgical microscope.

As soon as the voice operating module 2 is active, both sets of surgical microscope functions can be selected by voice command and, according to the present invention, certain continuous functions can then be operated by way of a keypad on the handle 4 or the foot controller 5, or by eye control 7. According to the present invention, the operating procedure for the surgeon is as follows: he or she switches on the voice operating module 2 by voice command, e.g. "Voice control on." He or she then selects the zoom function, e.g. by saying "Zoom," and is then able to operate the zoom by manual, foot, or eye controller. In a particular preferred embodiment, once operation of a function is taken over by a non-voice operating unit 4, 5, or 7, operation of that function is performed exclusively by the non-voice operating unit and cannot be performed via voice operating unit 2.

In another preferred embodiment of the invention, the voice operating unit 2 has an available "standby" mode in which all the functions of the surgical microscope can be operated conventionally by manual and/or foot and/or eye controller, for instance in the event of a failure of the voice operating unit 2 or the voice control system generally.

In yet another embodiment of the invention, the voice operating unit 2 has an available mode in which the continuous function(s) are executed as long as a certain sound (i.e. a vowel sound), is being uttered. A speaker-specific condition can also be provided, whereby the sound must be uttered by a certain individual. As soon as vocalization of that sound is halted, execution of the selected function is immediately stopped. Different sounds or different pitches correspond to different speeds of execution of the function. The voice operating module 2 can be connected to the control unit 6 via an electronic data line, in particular via a CAN bus and/or via light guide and/or a transmit/receive connection preferably with radio and/or light waves, in particular in the infrared region.

PARTS LIST

1 Operator
2 Voice operating module
3 Display for operating menu
4 Manual operating module (manual controller)
5 Foot-controlled operating module (foot controller)
6 Control unit
7 Eye-controlled operating module (eye controller)
8 Surgical microscope

What is claimed is:

1. A control apparatus for a surgical microscope having a set of discretely controlled functions and a set of continuously controlled functions, the control apparatus comprising:

a voice operating module; and at least one non-voice operating module;

wherein the voice operating module has a first mode in which the voice operating module i) selects and operates functions in the set of discretely controlled functions and ii) selects functions in the set of continuously controlled functions, and the non-voice operating module operates a selected function in the set of continuously controlled functions.

2. The control apparatus according to claim 1, wherein the voice operating module further has a second mode in which the voice operating module selects and operates functions in the set of discretely controlled functions and in the set of continuously controlled functions.

3. The control apparatus according to claim 1, wherein the voice operating module has a standby mode in which the non-voice operating module selects and operates functions in the set of discretely controlled functions and in the set of continuously controlled functions.

4. The control apparatus according to claim 2, further comprising a control unit connected to the at least one non-voice operating module, the control unit communicating with the surgical microscope to control functions in the set of continuously controlled functions.

5. The control apparatus according to claim 1, wherein the at least one non-voice operating module includes a manual operating module.

6. The control apparatus according to claim 1, wherein the at least one non-voice operating module includes a foot-controlled operating module.

7. The control apparatus according to claim 1, wherein the at least one non-voice operating module includes an eye-controlled operating module.

8. The control apparatus according to claim 4, wherein the control unit is also connected to the voice operating module and the control unit detects whether the voice operating module is in the first mode or the second mode.

9. The control apparatus according to claim 4, wherein the control unit is also connected to the voice operating module, and the voice operating module can be switched on and off both directly and via the control unit.

10. The control apparatus according to claim 4, wherein the voice operating module is remotely located with respect to the control unit.

11. The control apparatus according to claim 1, further comprising a display connected to the voice operating module.

12. The control apparatus according to claim 2, wherein functions in the set of continuously controlled functions are operated while a corresponding predetermined sound is being uttered to the voice operating module.

13. The control apparatus according to claim 12, wherein varied pitches of the predetermined sound correspond to varied execution speeds of the operated functions.

14. The control apparatus according to claim 1, wherein the voice operating module is remotely located with respect to a surgical microscope controlled thereby.

* * * * *